United States Patent [19]
Yacowitz

[11] Patent Number: 6,065,371
[45] Date of Patent: May 23, 2000

[54] DUAL NEEDLE INJECTION DEVICE

[76] Inventor: Harold Yacowitz, 221 Second Ave., Piscataway, N.J. 08854

[21] Appl. No.: 09/208,174

[22] Filed: Dec. 9, 1998

[51] Int. Cl.[7] ...................................................... B43K 5/00
[52] U.S. Cl. ............................................... 81/9.22; 30/362
[58] Field of Search ............................... 81/9.22; 30/362, 30/366; 606/118, 185

[56] References Cited

U.S. PATENT DOCUMENTS

| | | | |
|---|---|---|---|
| 4,204,438 | 5/1980 | Binaris et al. ............................. | 81/9.22 |
| 4,771,660 | 9/1988 | Yacowitz .................................. | 81/9.22 |
| 4,782,725 | 11/1988 | Spaulding ................................ | 81/9.22 |
| 5,054,339 | 10/1991 | Yacowitz .................................. | 81/9.22 |
| 5,165,488 | 11/1992 | Liu ........................................... | 173/49 |
| 5,496,304 | 3/1996 | Chasan ..................................... | 606/1 |
| 5,551,319 | 9/1996 | Spaulding et al. ....................... | 81/9.22 |

OTHER PUBLICATIONS

Spaulding & Rogers Brochure (Not sure if brochure is prior art, no date).

*Primary Examiner*—James G. Smith
*Assistant Examiner*—David B. Thomas
*Attorney, Agent, or Firm*—Walter J. Tencz, Jr.

[57] ABSTRACT

An improved injection apparatus is disclosed comprised of a first motor and a second motor, each motor having a shaft. First and second needles are located substantially perpendicular to the first and second shafts, respectively. When the first and second shafts rotate, the first and second needles, respectively, move up and down. The first and second shaft rotate in opposite directions. The first needle and second needles can be surrounded by first and second needle tubes, respectively. The first and second needle tubes can be mounted to a device housing. The first and second needles each preferably has a portion that lies inside its needle tube and a portion that lies outside its needle tube. First and second sources of liquid and first and second conveying tubes are provided. The first and second conveying tubes are connected to the first and second needles, preferably at a side arm inside the respective needle tubes. The first and second needles are preferably hollow. Preferably liquid flows from the first source of liquid to the first conveying tube then into the hollow first needle. Similar liquid flow occurs for the second needle. The first and second conveying tubes are connected to first and second meters which measure how much liquid is being fed into the first and second needles from the first and second liquid sources.

20 Claims, 6 Drawing Sheets

DUAL NEEDLE INJECTION DEVICE

FIELD OF THE INVENTION

This invention relates to improved methods and apparatus for using needles to insert fluids and suspensions of solids intradermally for purposes such as tattooing and delivering drugs vaccines, and other materials to the immune system and lymphatic system.

BACKGROUND OF THE INVENTION

High speed injection devices employing needles have been used for tattooing applications for many years. Various modifications to these devices were developed by the present applicant in U.S. Pat. No. 5,401,242 to Yacowitz; U.S. Pat. No. 5,054,339 to Yacowitz; and U.S. Pat. No. 4,771,660 to Yacowitz. These modifications enabled the delivery of drugs as well as pigments. Tattooing devices which are driven by magnetic coils as shown in those patents and in others have the problem of making a loud noise while they are operating. Relatively silent electric motor tattooing machines have been developed but the needle in those machines tends to drift in a single direction. This drifting effect makes it difficult to draw straight lines or to allow accurate delivery to specific skin areas. Present tattooing machines employ only one needle making the devices slow in completing an image.

SUMMARY OF THE INVENTION

The present invention in one embodiment provides a device for intradermally injecting fluids, and/or suspensions of solids. An apparatus is disclosed comprised of a first motor and a second motor. Each motor has a shaft. The apparatus is further comprised of a first and a second needle. Preferably the first and second needles are substantially perpendicular to the first and second shafts, respectively. When the first and second shafts rotate, the first and second needles, respectively, move up and down. Preferably the first and second shaft rotate in opposite directions. For example, if the first shaft rotates clockwise upon actuation of the first motor, the second shaft will rotate counterclockwise upon actuation of the second motor.

The first needle and second needles can be surrounded by first and second needle tubes, respectively. The first and second needle tubes can be mounted to a device housing. The first and second motor may have a motor housing which is mounted to the device housing.

In one embodiment first and second sources of liquid and first and second conveying tubes are provided. The first and second conveying tubes are connected to the first and second needles. The first and second needles are preferably hollow for drug delivery but can be solid with multiple points, for tattooing. Preferably liquid flows from the first source of liquid to the first conveying tube then into the hollow first needle. Similarly liquid flows from the second source of liquid to the second conveying tube then into the hollow second needle. A peristaltic pump is preferably used to move the liquid, but other types of pumps can also be used.

The first needle has first and second ends. The first needle also has a first portion which is surrounded by the first needle tube and a second portion which is not within the first needle tube. Preferably the second portion is relatively small so that only the "tip" of the first needle comes out of the first needle tube. The first conveying tube is preferably connected to the first portion so that the first conveying tube travels inside of and protrudes to outside of the first needle tube through a slot in the first needle tube. The second portion and first portion are hollow at least from a point where the first conveying tube is connected, all the way to the second end, or operating end, of the first needle. The connection between the second needle and the second conveying tube is analogous to the connection between the first needle and the first conveying tube.

In one embodiment of the present invention the first and second conveying tubes are connected to first and second meters which measure how much liquid is being fed into the first and second needles from the first and second liquid sources.

DETAILED DESCRIPTION OF THE DRAWINGS

Figure 1:
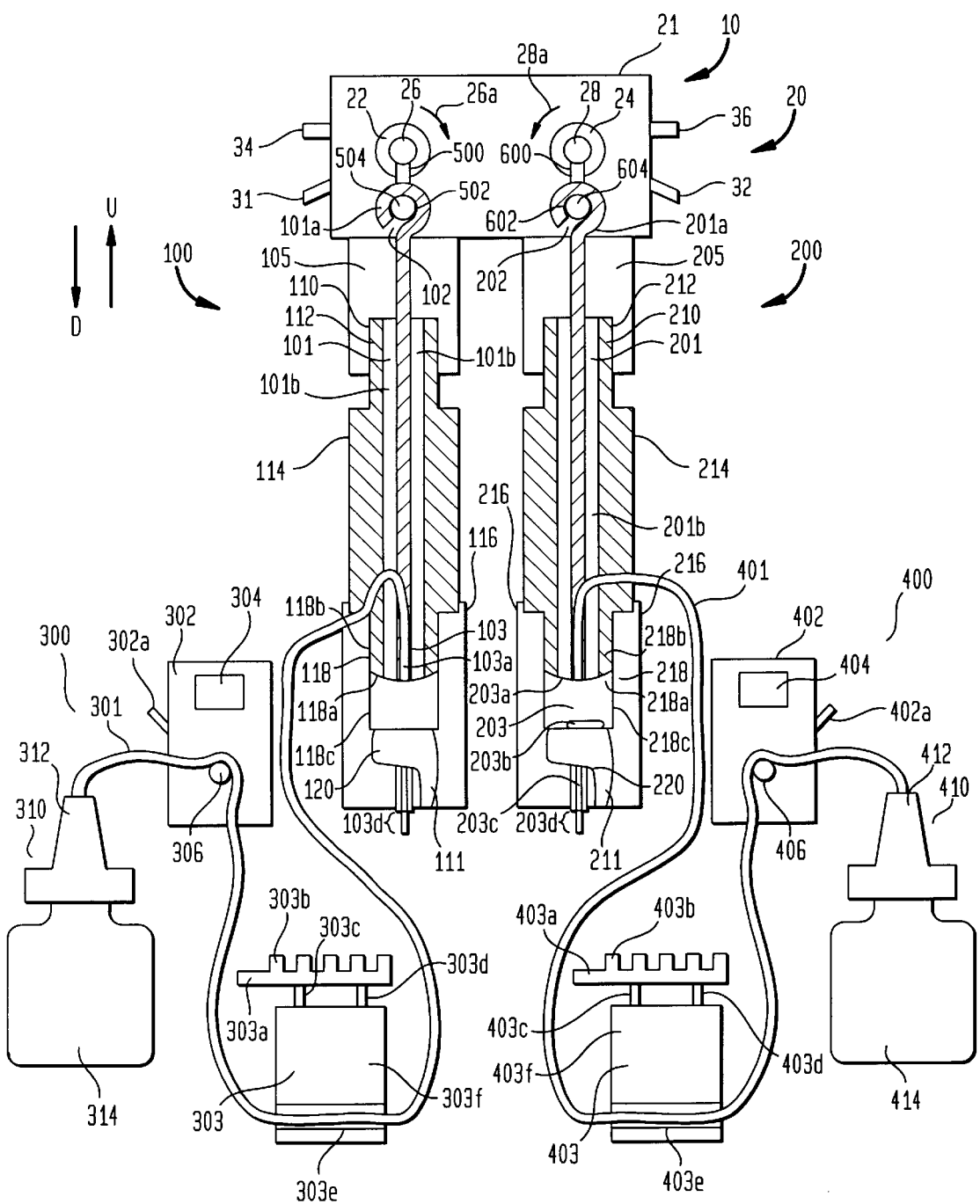
FIG. 1 shows an injection apparatus in accordance with an embodiment of the present invention.
Figure 7:
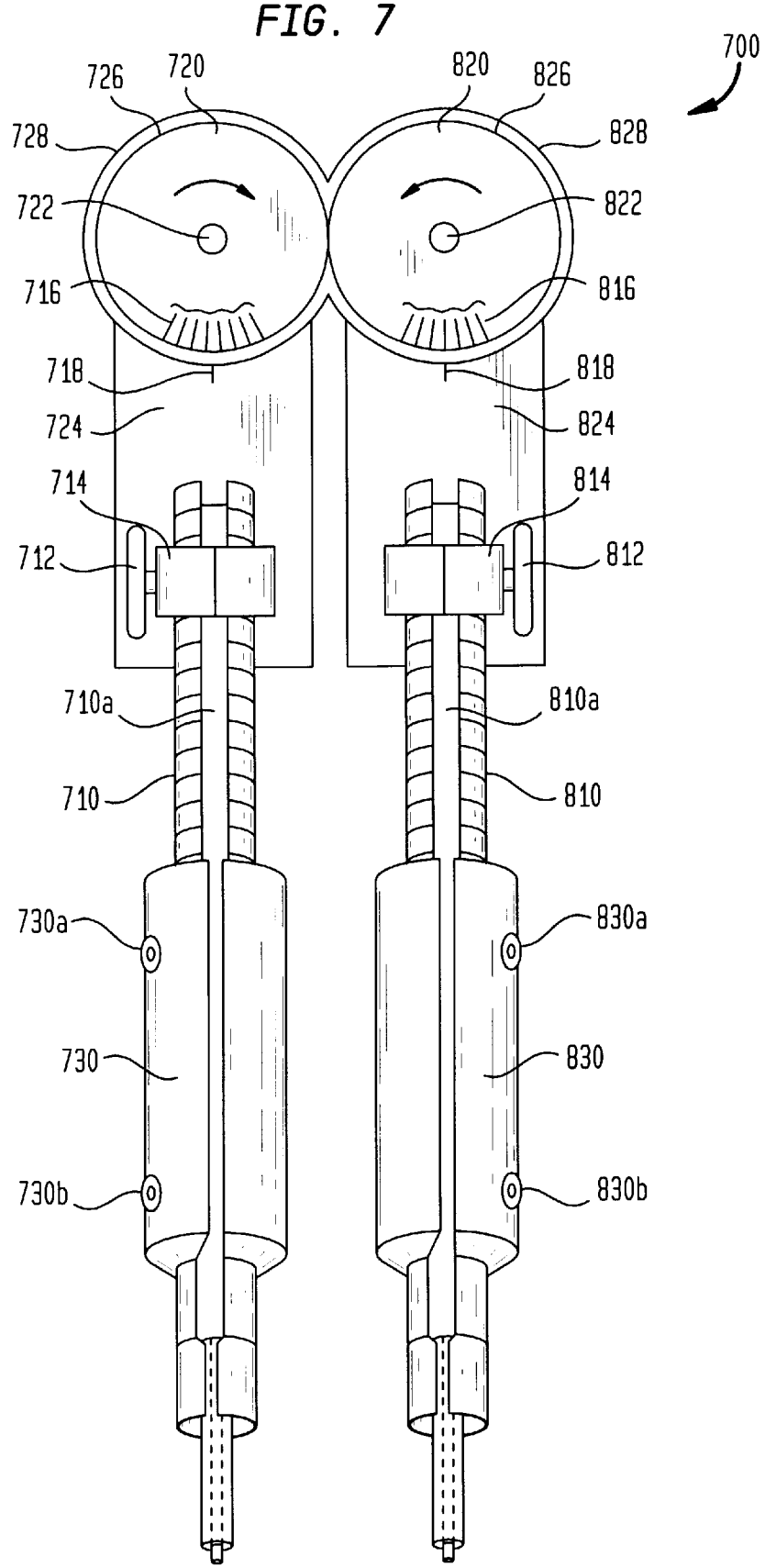
FIG. 7 shows a dual needle apparatus wherein an angle between the needles can be adjusted.
Figure 8:
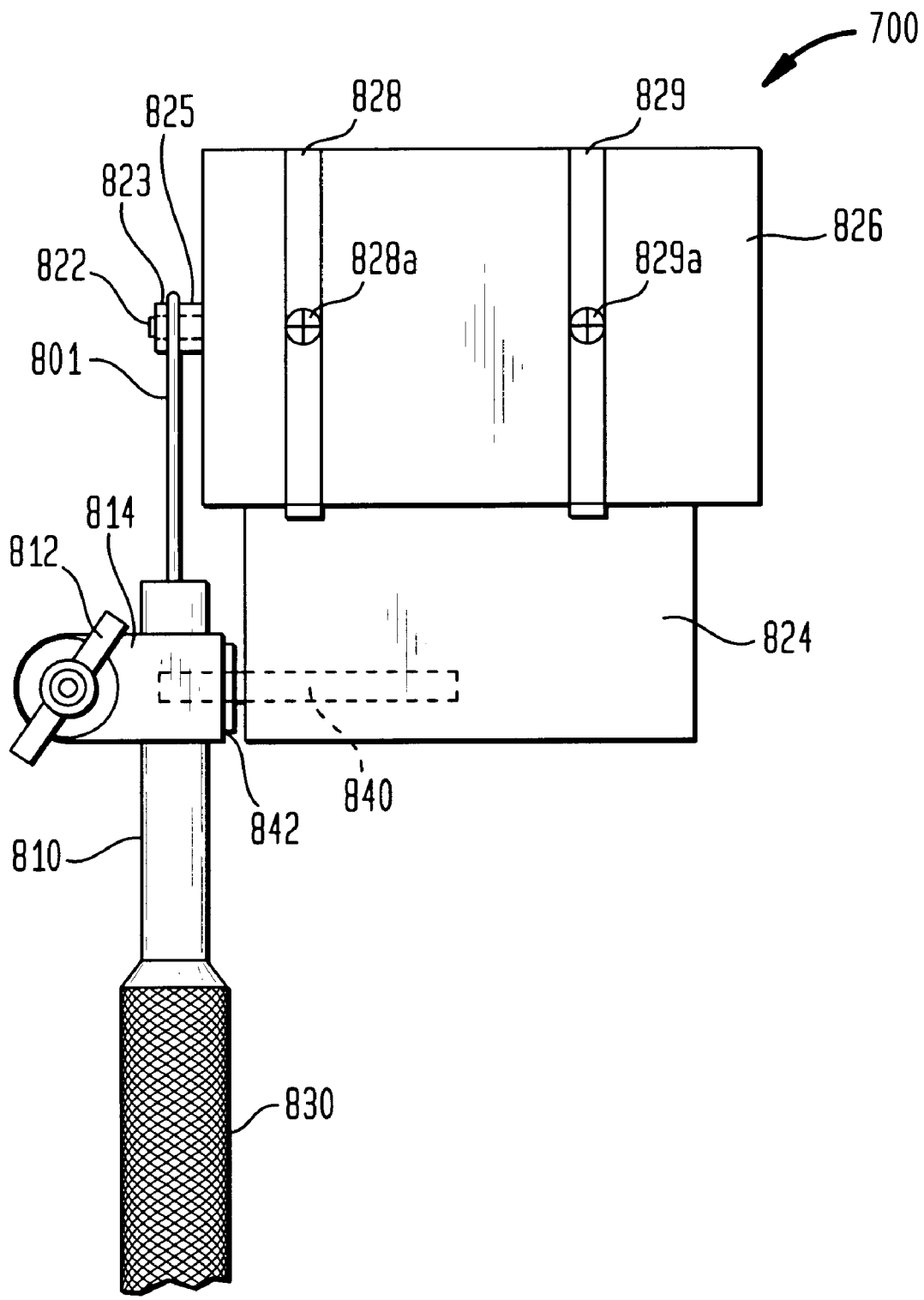
FIG. 8 shows a side view of a clamping device for a needle.

FIG. 1 shows an injection apparatus 10 in accordance with an embodiment of the present invention. The injection apparatus 10 includes motor device 20, left needle apparatus 100, right needle apparatus 200, left needle dispensing apparatus 300, and right needle dispensing apparatus 400. The motor device 20 includes motor device housing 21. The motor device housing 21 can be attached to needle tubes 110 and 210 by housing 105 and housing 205 respectively. The housing 105 and 205 are similar to housing 724 and 824 as shown in FIGS. 7 and 8. The motor device housing 21 and other housing (105 and 205 can be thought of as being part of the overall device housing.

The motor device 20 includes motor 22 which when actuated preferably causes a shaft 26 to rotate in a clockwise direction. The motor device 20 also includes motor 24 which when actuated preferably causes a shaft 28 to rotate in a counter-clockwise direction which is opposite that of the rotation of shaft 26. The direction of rotation is shown by the arrows 26a and 28a. The motors 22 and 24 are connected to motor device housing 21. The motors 22 and 24 can be turned on by switches 31 and 32 respectively. The speed of motors 22 and 24 can be adjusted by knobs 34 and 36, respectively.

Cams 500 and 600 are connected to shafts 26 and 28 of the motors 22 and 24 respectively. On cam 500 a roller 502 is rotatably mounted on axle 504. On cam 600 a roller 602 is rotatably mounted on axle 604. A loop area 101a of the needle 101 is rotatably connected around the roller 502. A loop area 201a of the needle 201 is rotatably connected around the roller 602. When the shaft 26 of the motor 22 turn in the clockwise direction 26a, the cam 500 on shaft 26 rotates clockwise. The roller 502 shown in FIG. 1 moves translationally clockwise about the shaft 26 with the cam 500 (upwards and leftwards from the position shown in FIG. 1) In addition to moving translationally, the roller 502 also rotates about the axle 504, while moving translationally. The needle 101 which is connected to the roller 502, also moves translationally about the shaft 26 (initially upwards and leftwards from the FIG. 1 position). The rotation of the shaft 26 thereby causes the needle 101 to go up and down. The shaft 28 of the motor 24, the cam 600, roller 602, and axle 604 function in the same manner as the shaft 26 and other related components with the exception that the shaft 28 moves in the counterclockwise direction 28a.

Figure 2:
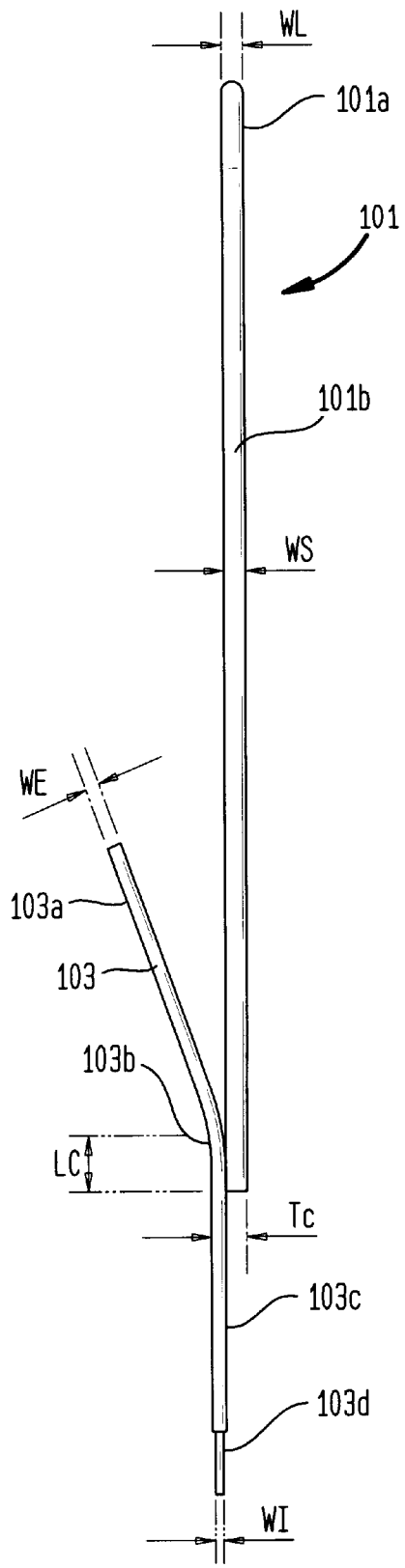
FIG. 2 shows a side view of a needle for use with the injection apparatus of FIG. 1.

The left needle apparatus 100 is comprised of left needle 101 and needle tube 110. The left needle 101, is shown in side view in FIG. 2, and includes a loop area 101a, shaft portion 101b, and side arm 103. The side arm 103 includes bent portion 103a, connected portion 103b, extension portion 103c, and tip portion 103d. The width of the loop area 101a, WL, can be approximately five millimeters and the width of the shaft portion 101b, WS, can be approximately 1–1.5 millimeters. The width of the extension 103a, WE, is variable and depends on the gauge of the needle, such as needle 101 being used. The width of the connected portion 103b of the side arm 103 together with the shaft portion 101b to which it is connected and which is shown as Tc, may be two to ten millimeters approximately. The length of the connected area of the side arm 103 with the shaft portion 101b, LC, may be a few millimeters. The length of the needle tip, LT, shown in FIG. 3, may be a few millimeters and will vary. The width of the tip 103d, which is shown in FIG. 2 as W1, is variable and depends on the gauge of the needle, such as needle 101, being used. The loop area 101a has a gap 102 shown in FIGS. 1 and 3. The loop area 101a is manufactured from a rod by simple bending. A closed loop would require welding and be more expensive but not any better. The open loop reduces manufacturing cost. The portion 103b is soldered to the shaft 101b, as shown in FIG. 2, but could be connected in some other manner.

The right needle apparatus 200 is comprised of right needle 201 and needle tube 210. The right needle 201 is preferably similar to the left needle 101 and is comprised of a loop area 201a, a shaft 201b, and a side arm 203. The side arm 203 is comprised of a bent portion 203a, a connected portion 203b, and extension portion 203c, and a tip 203d, shown in FIG. 1 and analagous to that of FIGS. 2 and 3.

The sidearm 103, which is part of the left needle 101, lies inside the needle tube 110. Preferably only the tip 103d lies outside the needle tube 110 (although how much lies outside the needle tube 110 depends on where the roller 502 is translationally in its rotation cycle. The same applies to sidearm 203 and tip 203d of right needle 203.

The needle tube 110 includes portions 112, 114, 116, 118, and 120. Portion 112 is an inner tube to hold the needle. Portion 112 includes graduations known in the prior art for setting penetration depths. Portion 114 is a knurled grip to be held by an operator of the injection apparatus 10. Portion 116 is a transparent plastic sleeve or plastic skirt covering which surrounds the needle 101 and surrounds the needle tip 103d, except at instances when the needle tip 103d protrudes outwards during its cycle of up and down movement. Skirt portion 116 protects the operator from having his fingers splashed by the drugs, vaccines or the like, being delivered. The skirt portion 116 also prevents splashing of the material being delivered on the skin adjacent to the injection site. Portion 118 is the bottom of the needle tube 110, it keeps the needle in position as it moves up and down, and it ends in a more narrow hole. Portion 118 includes curve 118a which separates the section 118b from the section 118c. Portion 120 is preferably internally even more narrow (can be approximately 1 millimeter) in internal diameter and keeps the tip of the needle (i.e. portion 103d) in position. The portion 120 has a square hole, which is a feature which is known. The square hole portion 120 allows the needle to stay in place. Partly surrounding portion 120 is a guide 111, which allows one to set the depth of penetration of the needle 101. A similar guide 211 is on the right needle tube 210. A guide 92 shown in FIG. 6 of U.S. Pat. No. 5,401,242 can be used and is incorporated by reference. The guide 111 can be adjusted up or down along with the needle tube 110 to provide a certain depth of penetration into the skin of the needle 101 and more specifically of the needle tip 103d. A procedure for adjustment of guide 111 is described in prior U.S. Pat. No. 5,401,242, col. 3, lns. 35–58 (in that patent a comparable guide is referred to as guide 92) which is incorporated by reference in this application.

The right needle apparatus 200 has components analagous to the left needle apparatus 100, except for changes in numbering. The right needle apparatus 200 includes right needle 201 and needle tube 210. The components of right needle 201 have been described with reference to left needle 101. The right needle tube 210 includes portions 212, 214, 216, 218, and 220 analagous to portions 112, 114, 116, 118, and 120 as shown in FIG. 1.

The left needle dispensing apparatus 300 is comprised of left pump and meter 302, left container 310, left conveying tube 301, and left pinch valve 303. The left pump and meter 302 is comprised of digital readout 304 and pump 306. The left container 310 is comprised of cap 312 and main portion 314. Similarly the right needle dispensing apparatus 400 is comprised of right pump and meter 402, right container 410, right conveying tube 401, and right pinch valve 403. The right pump and meter 402 is comprised of digital readout 404 and pump 406. The right container 410 is comprised of cap 412 and main portion 414.

Figure 3:
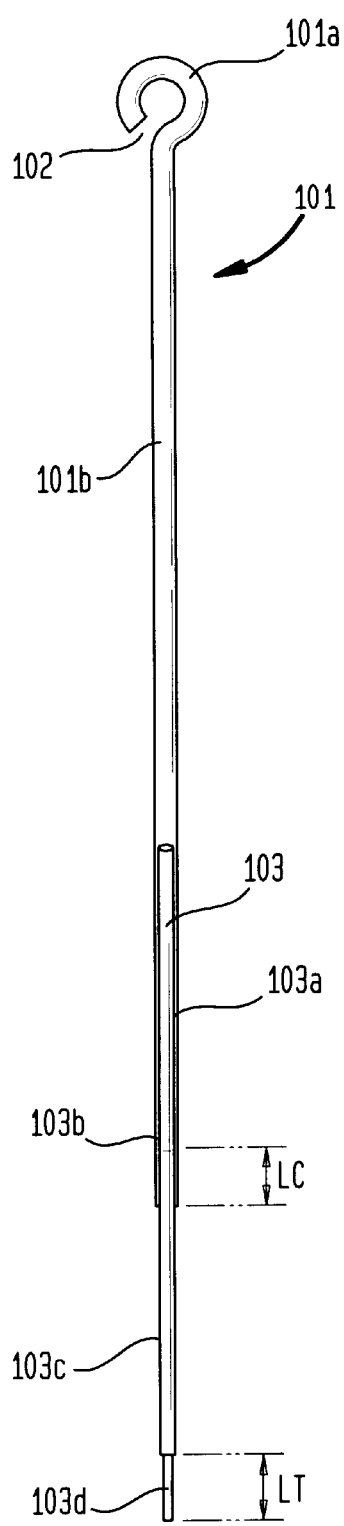
FIG. 3 shows a front view of the needle of FIG. 2.

The left conveying tube 301 is connected to the left needle side arm 103 at the bent portion 103a of the needle 101. The right conveying tube 401 is similarly connected to the right needle side arm 203 at the bent portion 203a of the needle 201 as shown by FIGS. 1, 2, and 3.

Figure 4:
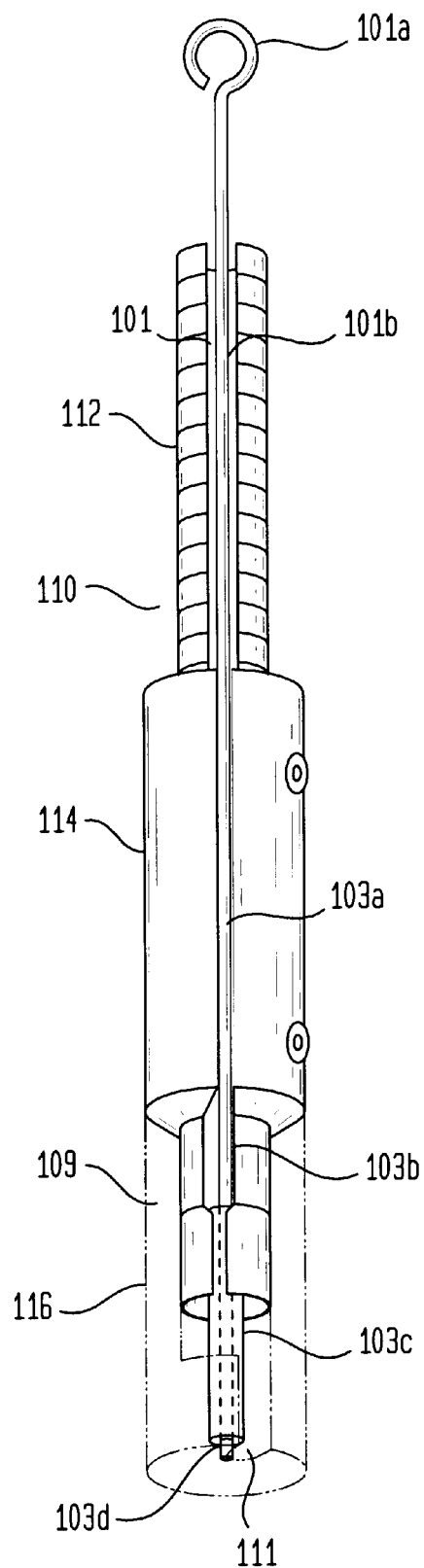
FIG. 4 shows a front view of the needle of FIG. 2 inside a needle tube in accordance with an embodiment of the present invention.
Figure 5:
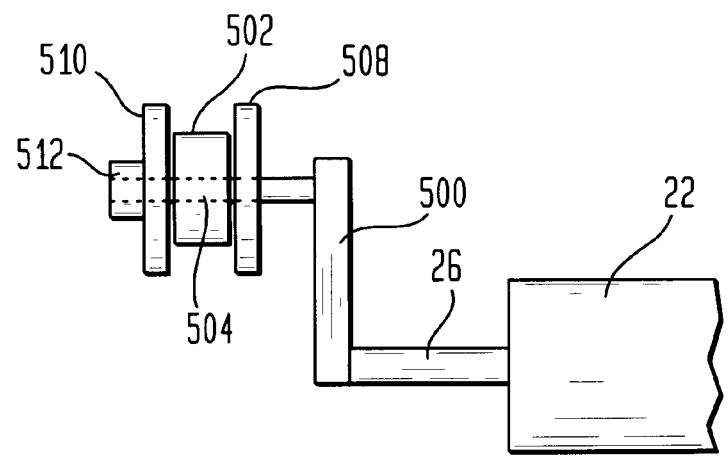
FIG. 5 shows a motor and related apparatus for use in moving a needle in the embodiment of FIG. 1.

FIG. 4 shows a front view of the left needle 101 and the needle tube 110 by themselves. FIG. 5 shows a side view of the motor 22 and related components. FIG. 5 shows the shaft 26 which is connected to the cam 500. The cam 500 is shown connected to the axle 504 upon which is mounted the roller 502. A washer 508 is shown in front of the roller 502 and a washer 510 is shown behind the roller 502. A cap 512 or nut holds the roller 502 onto the axle 504.

Figure 6:
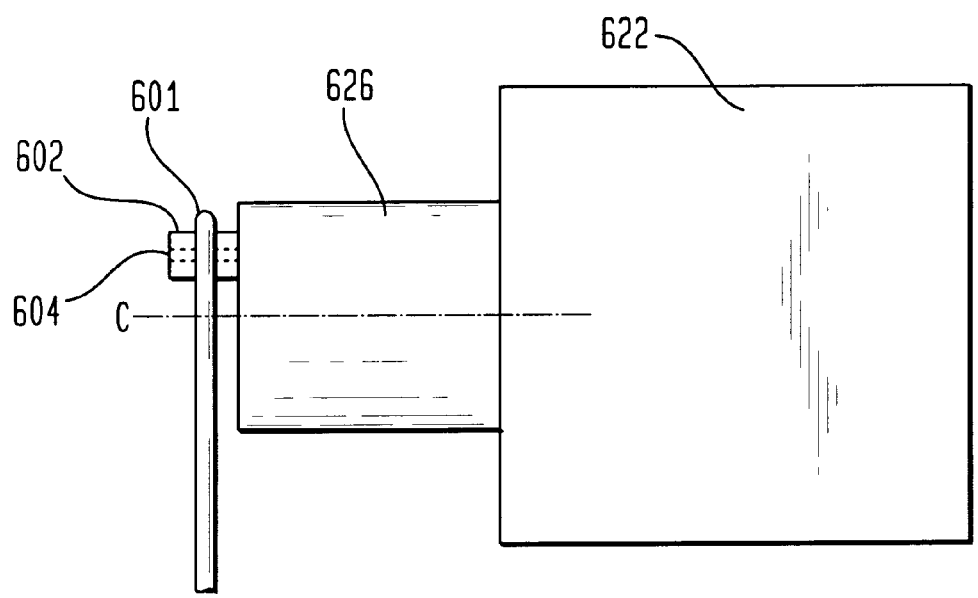
FIG. 6 shows an alternative apparatus for moving a needle.

FIG. 6 shows an alternative embodiment of a motor for use in accordance with the present invention. FIG. 6 shows motor 622 which has a shaft 626. On the shaft 626 a roller 602 is rotatably mounted on the top part of the shaft 626. The roller 602 is held on by an axle 604. A needle 601 (analagous to needle 101 or 201) is looped over the roller 602. FIGS. 5 and 6 shown a sketch of the inner workings of the motor, i.e. of the cam 500 and related components. Reduction gears can be included in the motor drive system, if desired, to increase force on needles. Reduction gears to increase or decrease force of a turning device are well known to mechanical engineers and need not be described. These are called reduction gears and they decrease speed and increase force.

In operation, a user can turn on the motors 22 and 24 by activating the switches 31 and 32, respectively. The switches 31 and 32 can also be foot switches. Activating the switch 31 causes shaft 26 of motor 22 to rotate in a clockwise direction and activating switch 32 causes shaft 28 of motor 24 to rotate in a counter clockwise direction, as shown by direction arrows 26a and 28a. The turning of shaft 26 clockwise causes needle 101 to move up and down in the directions U and D as shown in FIG. 1. Likewise, the turning of shaft 28 counterclockwise causes the needle 201 to move up and down in the directions U and D as shown in FIG. 1. Note that during operation, the needle tip 103d (or 203d) preferably protrudes out from guide 111 (or guide 211) only 0.1 to three millimeters.

Next switches 302a for the left pump and meter 302 and switch 402a for the right pump and meter 402 can be activated. Activating switch 302a causes liquid in liquid container 310 to flow through conveying tube 301 through pumping device 306, through pinch valve 303 and into the side arm 103 of the needle 101. Similarly, activating switch 402a causes liquid in liquid container 410 to flow through conveying tube 401 through pumping device 406, through pinch valve 403 and into the side arm 203 of the needle 201. The pinch valves 303 and 403 preferably each include attached heat sinks 303a and 403a, respectively. The pinch valves 303 and 403 also include heat sink vanes 303b and 403b, connecting screws 303c–d, and 403c–d, pinch valve areas 303e and 403e, and solenoids 303f and 403f. The heat sinks 303a and 403a include vanes, such as vane 303b and vane 403b which dissipate heat. The vanes 303b and 403b have to be fastened tightly against the metal portion of the valve in order to conduct heat away from the valve. The vanes 303b and 403b act to conduct heat and dissipate heat. Otherwise the pinch valves 303 and 403 can overheat and be destroyed. The heat sinks 303a and 403a may be made of stainless steel and are similar to older type house radiators. The pinch valves 303 and 403 allow fluid to enter into the needle 101 or needle 201 only when the needles are in the down position i.e. the tips 103d and 203d are pointing towards the skin of the person. An electrical switching device can be used to turn the pinch valves 303 and 403 on and off and can be connected to the drive mechanism, or left pump and meter 302 or right pump and meter 402. The pinch valves 303 and 403 are normally closed. When activated, they open and allow liquid to flow.

The present invention in one embodiment advantageously does not result in drifting as do present single motor electric motor machines because these machines do not have two motors which balances angular momentum (i.e in on embodiment of the present invention one motor rotates clockwise and one rotates counterclockwise to balance and inhibit drifting.

The needles can be driven at different speeds, i.e. needle 101 can be driven at one speed while the needle 201 can be driven at another speed. Knobs 34 and 36 can be used to adjust the first motor 22 speed and the second motor 24 speed, respectively. The setting of different speeds also allows the delivery of different amounts of drugs to different areas. In the case of tattooing, the fast moving motor (such as either motor 22 or motor 24 if desired) will result in a solid line while the slow moving motor will result in a dotted line. Various combinations of lines can produce aesthetic graphic designs.

In addition, by coupling separate liquid containers (such as liquid container 310 and 410, in FIG. 1) to each needle (such as needles 101 and 201) the apparatus 10 can be used to deliver several different pigments or different drugs in one operation.

The apparatus 10 is silent as compared with electromagnetic machines which are very noisy. Although hollow needles are preferred for drug delivery, solid needles can be used for tattooing with a dual motor (motors 22 and 24) embodiment of the present invention.

The entire apparatus 10 is preferably hand held and can be moved along the skin surface with the needles contacting the skin.

Motors 22 and 24 can be DC (direct current) or AC (alternating current). The motor housing 21 can be of durable plastic.

The pinch valves 303 and 403 can be solenoid pinch valves which are well known in the trade.

The spacing and/or angle between the needle tubes 110 and 210 in FIG. 1 can be varied slightly by incorporating the features of the embodiment of FIGS. 7 and 8, which will be described.

Depth of penetration of the needles is adjustable. By moving the needle tubes up 110 or 210 up or down and by use of the guide 92 shown in FIG. 6, incorporated by reference herein, of U.S. Pat. No. 5,401,242.

The angle of injection can be varied at will. When needle tubes 110 and 210 are adjusted inward or outward, (if features of FIGS. 7 and 8 are incorporated the injection angle changes. This allows for more quantitative delivery of drugs and aesthetic graphics when used for tattooing.

The skirt 116 on the working end of the needle tube 110 in FIG. 1 and FIG. 4 prevents splashing of the drug from the skin on to the operator, and also keeps the drug confined to the injection site thus providing safer operation.

Depth can be adjusted by moving the needle tubes 110 or 210 up or down and setting the guide 111, as explained in U.S. Pat. No. 5,401,242, col. 3, lns. 35–60 (guide numbered 95 therein) incorporated by reference herein.

This patent incorporates by reference U.S. Pat. No. 5,401,242 to Yacowitz; U.S. Pat. No. 5,054,339 to Yacowitz; and U.S. Pat. No. 4,771,660 to Yacowitz.

FIG. 7 shows a dual needle apparatus 700 wherein an angle between needle tubes 710 and 810 (and thus the needles therein) can be adjusted. The ability to adjust angles may be incorporated into the device of FIG. 1, but is shown separately in FIG. 7 to more precisely describe the angle changing (or spacing) capability. The needle apparatus 700 is comprised of needle tubes 710 and 810 which may be the same as needle tubes 110 and 210. The needle tubes 710 and 810 have spaces 710a and 810a through which needles can be inserted in the manner shown in FIG. 1. The needle tubes 710 and 810 are fixed to housing 724 and 824. The needle tubes 710 and 810 along with their respective housing can be rotated such that the lines 718 and 818 can be moved to different angle graduations 716 or 816. The graduations 716 or 816 allow one to set specific angles between the motors 726 and 826 and the needle tube housing 724 and 824. This allows major changes in angle of penetration and widens the space between the two needle tubes 710 and 810. The apparatus 700 also includes the screws 712 and 812 which go through clamp devices 714 and 814. The thumb screws 712 and 812 are used to clamp in the needle tubes 710 and 810 respectively. The clamp devices 714 and 814, which can be tightened by the thumb screws 712 and 812, may be split clamps which are well known in the tattooing field and have been used on most tattooing machines over the last ninety years. Again the FIG. 7 embodiment is preferably incorporated with the FIG. 1 embodiment. The needle tubes 710 and 810 and their respective housings 724 and 824, can rotate about the motors 726 and 826, respectively because needle tube housings 724 and 824 are held to the motors 726 and 826 by spring clamps 728 and 828. The apparatus 700 also includes grip 730 held to needle tube 710 by screws 730a and 730b and grip 830 held to needle tube 810 by screws 830a and 830b. All of these components can be incorporated with the FIG. 1 embodiment.

FIG. 8 shows a partial right side view of the apparatus 700 with a needle 801 inserted in the needle tube 810. Although the right side is described, the left side (for needle 701, not shown and needle tube 710 which be similar to needle 801 and needle tube 810). The needle 801 is attached to shaft 822. The shaft 822 rotates when activated by motor 826. The needle 801 may be of the same type shown in FIGS. 1–3. The needle 801 lies inside of the needle tube 810. The grip 830, thumb screw 812, and clamp 814 is shown. A bolt 840, shown in dashed lines, is imbedded in clamp 814 and in housing 824 and the bolt 840 fixes the needle tube 810 to the housing 824. The bolt 840 is threaded and includes on it a nut 842 which can be rotated to force the needle tube 810 closer to the housing 824 or farther away from the housing 824 which results in small changes in the angle of penetration of needle 801. Spring clamps 828 and 829 clamp the housing 824 to the motor 826. The spring clamps 828 and 829 are held to the motor 826 by screws 828a hand 829a respectively, which can be unscrewed to change the angle between the needle tubes 710 and 810 shown in FIG. 7, and the angle of penetration of the needle 701 in needle tube 710 not shown and needle 801 in needle tube 810 (shown in FIG. 7). One changes the angle of penetration for example for needle tube 810 in FIG. 8, by loosening screws 828a and 829a and then rotating the needle tube 810 and housing 824 to the desired position, so that line 818 (in FIG. 7) is facing directly across from one of the graduation lines 816. There are also washers 823 and 825 about both sides of the needle 801 on the shaft 822 which hold the needle 801 in place on the shaft 822.

I claim:

1. An apparatus comprised of:
   a first motor having a first shaft;
   a second motor having a second shaft;
   a first needle, having a first end and a second end, the first needle connected to the first shaft at its first end such that the first needle is substantially perpendicular to the first shaft, the first needle having a tip at its second end;
   a second needle, having a first end and a second end, the second needle connected to the second shaft at its first end such that the second needle is substantially perpendicular to the second shaft, the second needle having a tip at its second end;
   wherein the first motor can be activated to cause the first shaft to rotate clockwise and the first needle to vibrate up and down in response to the clockwise rotation of the first shaft;
   and wherein the second motor can be activated to cause the second shaft to rotate counter-clockwise and the second needle to vibrate up and down in response to the counter-clockwise rotation of the second shaft.

2. The apparatus of claim 1 and further comprising:
   a device housing;
   a first needle tube surrounding the first needle;
   a second needle tube surrounding the second needle;
   wherein the first and second needle tubes are mounted to the device housing;
   the first motor has a motor housing which is part of the device housing; and
   the second motor has a motor housing which is part of the device housing.

3. The apparatus of claim 1 and wherein:
   the first needle is comprised of:
   a loop area;
   a shaft;
   and a sidearm which is further comprised of a bent portion, a connecting portion and a tip portion;
   the connecting portion of the sidearm connected to the shaft of the first needle;
   and the loop area of the first needle is connected to the first shaft of the first motor.

4. The apparatus of claim 3 and wherein:
   the second needle is comprised of:
   a loop area;
   a shaft;
   and a sidearm which is further comprised of a bent portion, a connecting portion, and a tip portion;
   the connecting portion of the sidearm connected to the shaft of the second needle;
   and the loop area of the second needle is connected to the second shaft of the second motor.

5. The apparatus of claim 1 and further comprised of:
   a first conveying tube having a first end connected to the first needle and a second end connected to a first liquid source.

6. The apparatus of claim 5 and further comprised of:
   a second conveying tube having a first end connected to the second needle and a second end connected to a second liquid source.

7. The apparatus of claim 5 and wherein:
   the first needle has a hollow portion;
   and the first end of the first conveying tube is connected to the hollow portion of the first needle.

8. The apparatus of claim 6 and wherein:
   the second needle has a hollow portion;
   and the first end of the second conveying tube is connected to the hollow portion of the second needle.

9. The apparatus of claim 3 further comprised of:
   a first conveying tube having a first end connected to the first needle and a second end connected to a first liquid source;
   wherein the side arm of the first needle is hollow, and the first conveying tube is connected to the side arm at the bent portion of the side arm.

10. The apparatus of claim 9 further comprised of:
    the second needle is comprised of:
    a loop area;
    a shaft;
    and a sidearm which is further comprised of a bent portion, a connecting portion, and a tip portion;
    the connecting portion of the sidearm connected to the shaft of the second needle;
    and the loop area of the second needle is connected to the second shaft of the second motor;
    further comprised of a second conveying tube having a first end connected to the first needle and a second end connected to a first liquid source;
    wherein the side arm of the second needle is hollow, and the second conveying tube is connected to the side arm at the bent portion of the side arm.

11. The apparatus of claim 5 further comprised of:
    a first pinch valve;
    the first pinch valve separating the first conveying tube into two parts, the first part of the conveying tube connected to the first liquid source, the second part of the first conveying tube connected to the first needle;

wherein the first pinch valve allows liquid to be transmitted from the first liquid source through the first conveying tube into the first needle when the tip of the first needle moves down substantially towards the skin, and the first pinch valve does not allow liquid to be transmitted from the first liquid source through the first conveying tube into the first needle when the tip of the first needle is not substantially moving down towards the skin.

12. The apparatus of claim 11 further comprised of:

a second conveying tube connected to the second needle;

a second pinch valve;

the second pinch valve separating the second conveying tube into two parts, the first part of the second conveying tube connected to a second liquid source, the second part of the second conveying tube connected to the second needle;

wherein the second pinch valve allows liquid to be transmitted from the second liquid source through the second conveying tube into the second needle when the tip of the second needle moves substantially towards the skin, and the second pinch valve does not allow liquid to be transmitted from the second liquid source through the second conveying tube into the second needle when the tip of the second needle is not substantially moving towards the skin.

13. The apparatus of claim 2 further comprised of:

a first skirt which surrounds the tip of the first needle;

and a second skirt which surrounds the tip of the second needle.

14. The apparatus of claim 1 wherein:

the first and second needles are solid.

15. The apparatus of claim 1 wherein:

the first and second needles can be adjusted to be parallel to one another or to be at angle with respect to one another.

16. The apparatus of claim 1 and wherein:

the speed of the first motor can be adjusted without adjusting the second motor speed and;

the speed of the second motor can be adjusted without adjusting the first motor speed.

17. The apparatus of claim 1 and further comprising:

a first pumping system for delivering material to the first needle; and a first display for displaying the amount of material delivered by the first pumping system to the first needle.

18. The apparatus of claim 17 and wherein:

the first display is digital.

19. The apparatus of claim 17 and further comprising:

a second pumping system for delivering material to the second needle; and a second display for displaying the amount of material delivered by the second pumping system to the second needle.

20. The apparatus of claim 19 and wherein:

the first and second displays are digital.

* * * * *